United States Patent [19]

Lubetzky et al.

[11] Patent Number: 5,531,995
[45] Date of Patent: Jul. 2, 1996

[54] LOW ECOTOXIC FORMULATIONS OF PESTICIDES

[75] Inventors: David Lubetzky, Lehavim; Maurice Frances, Beer Sheva, both of Israel

[73] Assignee: Makhteshim Chemical Works Ltd., Beer-Sheva, Israel

[21] Appl. No.: 375,707

[22] Filed: Jan. 20, 1995

Related U.S. Application Data

[63] Continuation-in-part of Ser. No. 988,800, Dec. 10, 1992, abandoned.

[30] Foreign Application Priority Data

Oct. 29, 1992 [IL] Israel ......................................... 103585

[51] Int. Cl.$^6$ .................................................. A01N 25/08
[52] U.S. Cl. .................................................. 424/409
[58] Field of Search ............................ 424/409; 514/443

[56] References Cited

U.S. PATENT DOCUMENTS

| | | |
|---|---|---|
| 2,291,205 | 7/1942 | Borglin . |
| 2,490,925 | 12/1949 | Schertz . |
| 3,658,813 | 4/1972 | Godefroi et al. . |
| 4,154,945 | 3/1979 | Brookes et al. . |
| 4,211,566 | 7/1980 | Matsuda et al. . |
| 4,549,027 | 10/1985 | Gates . |
| 4,957,533 | 9/1990 | Arnold et al. . |
| 5,057,326 | 10/1991 | Sampson . |
| 5,177,098 | 1/1993 | Benoit . |
| 5,304,376 | 4/1994 | Friedrichs et al. .............. 424/409 |

FOREIGN PATENT DOCUMENTS

| | | |
|---|---|---|
| 0432061 | 11/1990 | European Pat. Off. . |
| 0432062 | 11/1990 | European Pat. Off. . |
| 1044663 | 6/1963 | United Kingdom . |
| 1382894 | 10/1972 | United Kingdom . |
| 1398227 | 11/1972 | United Kingdom . |
| WO9177657 | 11/1991 | WIPO . |

OTHER PUBLICATIONS

Miall's Dictionary of Chemistry, Longman Group Limited, Essex (UK), 1981, p. 405.

Y. Momotari, "Fungicidal compositions for agricultural use", Brit. 1,051,360, Dec. 14, 1966.

E. I. Levin, T. S. Belyaeva, I. P. Strelets, O. G. Timokhina, V. I. Grigorenko, M. K. Zhumabekov, V. R. Ishchenko, V. I. Petrova, "Sticky composition for eliminating household insects", SU 1,187,773, Oct. 30, 1985.

H. Miyato, S. Ito, E. Ogata, "Insecticidal compositions containing rosin and powders with the Zacher's effects against termites", JP 63,250,308, Apr. 6, 1987.

Z. Zhang, "Microbicidal, Insecticidal, and growth–prompting compositions for crops", CN 1,031,467, Mar. 8, 1989.

T. S. Belyaeva, et al, "Sticky composition for killing household insects", SU 733,596, May 15, 1980.

V. F. Smirnov, A. A. Anisimov, A. S. Semicheva, "Improving fungal resistance of the epoxy polymer", CA 86:156376, 1977.

K. Matsumoto, S. Sasaki, "Insect attractant compositions containing natural and synthetic rubbers", JP 76,19,132, Feb. 16, 1976.

Chemical Patents Index, Documentation Abstracts Journal, Week 9022, Derwent Publications Ltd., London, GB; AN 90–167886.

Central Patents Index, Basic Abstracts Journal, Week 7814, Derwent Publications Ltd., London, GB; An 78–26428A.

C.A. 111:92336A Miyato et al. Oct. 1988.

Derwent Abstract of JP 53 020431 Jan. 1993.

*Primary Examiner*—Peter F. Kulkosky
*Attorney, Agent, or Firm*—Browdy and Neimark

[57] ABSTRACT

There is provided an EW pesticidal formulation comprising:

(a) 190 g/l to 350 g/l of at least one pesticide selected from the group consisting of chlorpyrifos, endosulfan, and imazalil.

(b) 150 g/l to 400 g/l of the methyl ester of rosin.

(c) 30 g/l to 200 g/l of at least one surfactant.

(d) water to make up to one liter, but not less than 200 g/l; and optionally containing a polar solvent completely or partially soluble in water. This affords formulations which have low irritations and surprisingly improved biological activity to target species.

20 Claims, No Drawings

LOW ECOTOXIC FORMULATIONS OF PESTICIDES

This application is a continuation-in-part of the parent application Ser. No. 07/988,800 filed on Dec. 10, 1992 now abandoned, the contents of which are hereby incorporated by reference.

BACKGROUND OF THE INVENTION

The present invention relates to specific types of pesticidal formulations which are emulsions in water (hereinafter referred to as EW formulations). The present invention particularly relates to EW pesticidal formulations containing the methyl ester of rosin their preparation and their application to pesticides having low or medium melting points.

Solid pesticides having a low or medium melting point are generally commercialized as emulsifiable concentrate solutions. However, such formulations require considerable quantities of organic solvents and other ingredients, creating toxicological and ecotoxicological problems. Thus, the United States Environmental protection Agency has recently begun a review of the ingredients of pesticidal formulations other than the active ingredient. In Europe, the EEC Council is in an advanced stage of legislating into law volatile organic compounds (VOC) and to require the eco-labeling of formulations which contain such VOC's. Indeed, Canada and Germany already have a system of ecotoxic labelling.

Rosin and its derivatives have been known since ancient times and they have found safe uses for a wide variety of products, including food and cosmetics. Uses in agriculture are also known as follows.

Great Britain patent no. 1,044,663 describes the use of a rosin or its derivatives in organophosphorous insecticidal compositions, but said compositions require the use of organic solvents.

Great Britain patent number 1,382,894 describes the use of rosin or its derivatives in carbamic ester compositions, but said compositions also require the use of organic solvents. The same can be said for the compositions described in Great Britain patent number 1,051,360 (Chemical Abstracts, 66: 54559v) and Soviet Union patent number 733,596 (Chemical Abstracts, 93: 127147d).

Rosin or its derivatives have been reported to be a tackifier agent in pesticidal formulations, such as in Great Britain patent number 1,398,227; U.S. Pat. No. 4,211,566; and Soviet Union patent number 1,187,773 (Chemical Abstracts, 104: 10445a). In addition, rosin or its derivatives have also been reported in pesticidal powder formulations. Examples are: Japan Patent Kokai Publication number 76/19,132 (Chemical Abstracts, 84: 175194c);

Japan Patent Kokai Publication number 63/250,308 (Chemical Abstracts, 111: 92336a); and Chinese patent publication number 1,031,467 (Chemical Abstracts, 113: 19497r).

Rosin derivatives have been reported to improve the fungal resistance of polymers in Chemical Abstracts, 86: 156376p.

European patent publication numbers 432,061 and 432, 062 recently disclosed aqueous emulsions of a large variety of agrochemicals. However, said compositions did not require the use of rosin and still required the use of undesirable organic solvents.

U.S. Pat. No. 2,291,205 describes a formulation of a liquid pesticide (pine oil) using a metal salt of rosin for a liquid active ingredient and not a solid one. What works well for a liquid pesticide may not necessarily work for a solid pesticide in an EW formulation.

U.S. Pat. No. 2,490,925 describes a formulation where the rosin or rosin derivative is the active pesticide. In the present invention the rosin is used as a plasticizer. Thus, U.S. Pat. No. 2,490,925 is not relevant to the present invention.

U.S. Pat. No. 4,957,533 describes the use of—among a large number of compounds—rosin derivatives as solvents to formulations of a special group of compounds. But this patent does not exemplify a single case where rosin derivatives are used.

PCT Patent Number WO91/17,657 describes formulations of various pesticides using rosin as a plasticizer. However, most of the examples also use aromatic solvents. Only the examples with chlorpyrifos are relevant to the present inventions; and these examples are problematic. In Example K, if one increases the concentration of chlorpyrifos to the commercially useful concentration of 18–20%, will not work as there will then be no place for water. Example L also does not work as the use of 20% chlorpyrifos causes crystallization (as shown in the comparative Examples.

SUMMARY OF THE INVENTION

In accordance with the present invention there is provided an EW pesticidal formulation comprising:

(a) 190 g/l to 350 g/l of at least one pesticide selected from the group consisting of chlorpyrifos, endosulfan, and imazalil.

(b) 150 g/l to 400 g/l of the methyl ester of rosin.

(c) 30 g/l to 200 g/l of at least one surfactant; and (d) water to make up to one liter, but not less than 200 g/l.

The present invention optionally contains at least one polar solvent completely or partially soluble in water in the concentration of up to 200 g/l.

DETAILED DESCRIPTION OF THE INVENTION

In order that formulations of the present invention retain their ecological acceptability, it is preferable to use a surfactant in which the lipophillic part is safe natural product. Such surfactants are usually found in use in the food and cosmetic industries.

The surfactants of the present invention are those with an H.L.B. range of from 7 to 17, preferably from 10 to 15. Examples of such surfactants are alkoxylated triglycerides and alkoxylated sorbitol fatty esters. Preferred surfactants are alkoxylated triglycerides such as ethoxylated castor oil, ethoxylated propoxylated castor oil, and alkoxylated sorbitan fatty esters;

The novel formulations of the present invention may also contain:

an antifreeze;

an antifoam, such as polysyloxanes;

an emulsion stabilizer;

auxiliary additives.

As conventional antifreeze agents can be mentioned agents such as propylene glycol, glycerol, diethyl-lene glycol, triethylene glycol, or urea.

Examples of emulsion stabilizers are fumed and precipitated silica and alumino-silicates, bentonites and other swelling clays.

Organic compounds such as polysachrides of the xantam gum type, the alginates, the carboxylated or hydroxylated methyl-celluloses, the synthetic macromolecules of the polyvinyl-prolidone, polyethylene glycol, polyvinylic alcohol type, may also be used as emulsion stabilizers.

Auxiliary additives that may be used as oxidation and u.v. protectants, pH buffers, bactericides and A.I. stabilizers.

The concentrated EW formulations which are the object of the present invention, may be prepared as follows:

Mixing one or more molten pesticidal active ingredients with the plasticizer, adding one or more of the surfactants to the mixture and preparation of the emulsion following one of the standard methods of procedure. To this end one may use an apparatus such as high-sheer mixers, high pressure orifice homogenizers and the like.

These concentrated water emulsions of the present invention are stable physically and chemically in a temperature range from $-14°$ C. to $54°$ C., where no crystallization phenomena are observed during storage. They are also stable when diluted in water. These emulsions may also be used undiluted as ulv formulations or with low dilution (L.V. formulations).

The advantage of the present invention is that commercially viable concentrations of stable EW formulations of the pesticide may be used—that is, without any formation of crystals.

The present invention is also of particular mote, because the formulations related to it have a low degree of phytotoxicity compared to the commercial E.C. equivalents. They may also partially replace powder formulations, avoiding in this way all the dust problems vis-a-vis the user.

The EW formulations of the present invention have the further advantages of being non-flammable and of being of low dermal toxicity and low skin irritation.

Finally, the EW formulations of the present invention can be considered ecotoxicologically safe, since they are prepared with safe inert ingredients. The result is not only useful formulations, but also formulations which can stand up to the stringent requirements of the EPA in the United States and the stiff European control of volatile organic compounds.

While the invention will now be described in connection with certain preferred embodiments in the following examples, it will be understood that it is not intended to limit the invention to these particular embodiments. On the contrary, it is intended to cover all alternatives, modifications and equivalents as may be included with the scope of the invention as defined by the appended claims. Thus, the following examples, which include preferred embodiments, will serve to illustrate the practice of this invention, it being understood that the particulars shown are by way of example and for purposes of illustrative discussion of preferred embodiments of the present invention only and are presented in the cause of providing what is believed to be the most useful and readily understood description of procedures as well as of the principles and conceptual aspects of the invention.

EXAMPLE 1

To 210 g of molten endosulfan were added 190 g of Abalyn E (methyl ester of rosin ex Hercules) 100 gr of Soprophor 14-R (ethoxylated castor oil 60 EO ex R.P and 10 g of Epoxol 7-4 (epoxilated soybean oil—Swift). The mixture was then mixed until homogeneous. To 475 g of deionized water was added 5 g of Aerosil COK 84 (fumed silicon ex Degussa). A suspension was prepared in a homogenizer Ultron Turox 45 T. An emulsion was prepared afterwards adding progressively the aqueous suspension of Aerosil COK 84 into the organic mixture. 1 g of antifoam Silicon AF120 (ex AIDCHIM) is added during the operation. This operation lasts approximately 15 minutes with progressive increase of the agitation rate up to a maximum of 10,000 rpm. This emulsion had the following characteristics:

It is stable in a range of temperatures from $-14°$ C. to $54°$ C.

It showed no crystallization with time.

It remained stable when diluted in a rate of 5/100 (v/v) in CIPAC standard water D (no separated material or creamy settling is observed.).

EXAMPLE 2

The procedure of Example 1 was repeated, using ethyl chloropyrifos as active ingredient, as follows: 255 g of molten chloropyrifos ethyl, 255 g of Hydrogal M (Methyl ester of hydrogenated rosins, ex. D.R.T), 100 g of Soprophor 14-R, 1.2 g of Epoxol 7-4, 1 g of Silicaid AF 100, 5 g of Aerosil COK 84 suspended in deionized water to make up 1 liter. This emulsion had the following characteristics:

It is stable in a range of temperatures from $-14°$ C. to $54°$ C.

No crystallization with time.

Stable when diluted at 5% v/v in CIPAC standard water D.

EXAMPLE 3

The procedure described in Example 1 was repeated using 205 g of molten Imazalil, 180 g of Granolite M, 100 g of Servirox OEG 68.5, 1 g of antifoam Silicaid AF 100 and deionized water to make up to 1 liter of emulsion. This emulsion had the following characteristics:

Stable in a range of temperatures from $-14°$ C. to $54°$ C.

No crystallization with time.

Stable when diluted in a ration of 5% v/v in CIPAC standard water D.

EXAMPLE 4

A trial to check the relative phytotoxicity was carried out with endosulfan 20EW (Example 1) and commercial endosulfan 35 EC.

The trials were carried out with cucumbers in a greenhouse. The plants were sprayed once at 0.1% A.I. and the observation was done 6 days later. The results were as follows:

|  | Level of phytotoxicity |
|---|---|
| EW | 1 |
| EC-35 | 2 |
| Untreated | 0 |

Both formulations had some phytotoxicity, but the EW formulation of the present invention was less phytotoxic than the commercial EC.

EXAMPLE 5

The formulation of Example 2 was used to form an oil in water emulsion by mixing the appropriate amount of formulation with water to apply 50 g of chloropyrifos per 1000

$m^2$ in a spray volume of 100 liters per 1000 $m^2$. The results were compared with the results of commercial chloropyrifos 48 E.C. (Aromatic solvent). The emulsions were sprayed on vineyards against polychrosis botrann. In 20 bunches were counted the number of contaminated berries. The results, expressed as average number of infected spots per bunch and number of infected berries, are shown in the following Table:

| BIOLOGICAL ACTIVITY OF VARIOUS FORMULATIONS OF CHLOROPYRIFOS AGAINST *POLYCHROSIS BOTRANA* IN GRAPES | | |
| --- | --- | --- |
| | Number of Infected spots | Number of infected Berries |
| Chlorpyrifos EW | 1.00 D | 2.00 D |
| Chlorpyrifos aromatic | 1.75 B | 4.00 CD |
| Untreated | 7.25 A | 34.00 A |

EXAMPLE 6

Following the method of Example 5, similar tests were run but against *Pseudococcus s.p.* i grapes. The results were as follows:

| | Number of Infected Bunches |
| --- | --- |
| Chlorpyrifos EW | 0.25 c |
| Chlorpyrifos aromatic | 2.00 b |
| Untreated | 17.75 |

EXAMPLE 7

Insecticidal activity of chlorpyrifos formulations was tested at the Biological Institute on German cockroaches Blattella germanica (Dictyopera: Blattellidae) bred in the laboratory of the Ministry of Health in Jerusalem.

The pyrinex formulations tested are:

1. Regular sanitary formulation of 480 g/l a.i. EC.
2. Chlorpyrifos 250 a.i. EW
3. Untreated

Procedure

Ceramic tiles were dipped into an 0.5% a.i. solution of the formulation tested. After the water and solvent had evaporated from the surface, 2 tiles were placed on top of each other, separated by a cardboard, inside a plastic test cubicle. The test cubicle was 16×33×38.5 cm, with 4 air-openings, a sleeve to introduce food and water, covered by a glass plate. Each exposure experiment lasted 48 hours, with 4 repetitions on 25 to 50 cockroaches. This procedure avoided forced contact between the cockroach and the formulation-coated tile.

Results showing the activity of the different formulations are given in the Table below.

TABLE

BIOLOGICAL ACTIVITY OF CHLORPYRIFOS AGAINST *DICTYOPTERNA BLATTELLIDAE*
Percent Mortality of the Roaches

| | Number of Days After Spraying | | | | | | |
| --- | --- | --- | --- | --- | --- | --- | --- |
| Application | 14 | 28 | 42 | 56 | 77 | 91 | 107 |
| Chlorpyrifos EW | 100 | 98.9A | 99.1A | 93.4A | 95.5A | 93.0AB | 51.4B |
| Chlorpyrifos (aromatic) | 100 | 86.3B | 57.6B | 29.4B | | | |
| Untreated | 0.9C | 1.0C | 0.0C | 0.0C | 0.0C | 0.0C | 0.0C |

The closed prior art (WO 91/17,657) was checked out in the following comparative Example.

COMPARATIVE EXAMPLE 1

240 g of ethyl chlorpyrifos were melted together at 105° C. with 300 g of Staybelite 10 ester (glycerol ester of hydrogenerated rosin—ex Hercules). To the melt were added 30 g of Atlas G5000 (polyethylene glycol ether, HLB 16.9—ex ICI) and 30 g of Berol 822 (calcium dodecyl benzene sulfonate 60% A.1.—ex Berol).

This was mixed until an homogeneous liquid is obtained. An emulsion was prepared using an Ultra-Turax T-45 homogenizer by slow adding the organic mixture into 400 gr of hot water. The emulsion was cooled to room temperature. The resulting product was a water in oil emulsion (invert) which of course—can't be diluted in water and sprayed.

COMPARATIVE EXAMPLE 2

The procedure of example 1 was repeated using 240 g of chlorpyrifos, 300 g of Staybelite 10 ester, 30 g of Atlas G5000 30 gr of Berol 822, 20 gr of Sopraphor 14-R (ethoxylated castor oil 60 mol E.O.—ex R.P.) and 380 g of water. The resulting emulsion was excellent but very viscuous, almost not pourable.

COMPARATIVE EXAMPLE 3

The procedure of example 1 was repeated using 200 g of chlorpyrifos, 250 g of Staybelite 10 ester, 25 g of Atlas G5000 25 g of Berol 822, 15 gr of soprophor 14-R, 1 g of Kelzam (Xanthan gum—ex Kelco) and 485 g of water. This emulsion had the following characteristics: it is stable when stored for two weeks at 54° C. and at room temperature.

It remained stable when diluted (CIPAC MT 36) e.g. no separated material, nor creamy settling was observed after standing of 24 h at 30° C. After one week storage of the concentrate at 0° C. crystallization of the active ingredient was observed in a large amount. The crystallization was not reversible when the emulsion stayed at room temperature.

Such phenomenon is prohibitive especially in countries with cold climated when such temperatures are often reached.

COMPARATIVE EXAMPLE 4

The procedure of example 1 was repeated using 200 g of Chlorpyrifos, 250 of Staybelite 10 ester, 25 g of Pluronic PE 6400 (ethylene oxide/propylene oxide block polymer—ex BASF), of water. Immediate oil separation was observed, the emulsion was thus unacceptable.

COMPARATIVE EXAMPLE 5

The procedure of example 1 was repeated using 200 g of Chlorpyrifos, 20 g of Staybelite 10 ester, 30 g of Pluronic 6200 (ethylene oxide/propylene oxide block polymer—ex BASF), 120 g of Soprophor 14-R 450 g of water and 1 g of Kelzan. The resulting emulsion was very good. Nevertheless after one week at room temperature micro-crystals were observed, and the storage was discontinued. The product was unacceptable.

COMPARATIVE EXAMPLE 6

The procedure of example 1 was repeated using 185 of chlorpyrifos, 300 of Dertoline G 1 (glycerol ester of rosin—ex d.r.t.), 140 g of Emulan El (castor oil ethoxylate 36 mol. E.O—ex BASF) and 375 g of water. The resulting emulsion was extremely viscous.

COMPARATIVE EXAMPLE 7

Concerning example K of WO 91/17,657 one can see that a 20% A.I. formulation is not applicable, indeed if the relation between the coformulants is respected there is no place for water, thus:

| | |
|---|---|
| Chlorpyrifos | 20.0 |
| Rosin ester | 70.0 |
| Non-ionic surfactant | 3.6 |
| Dobenz - Ca | 6.3 |
| | 99.9% |

We claim:

1. A stable and non-separated EW pesticidal emulsion formulation consisting essentially of:
   (a) 190 g/l to 350 g/l of at least one pesticide selected from the group consisting of Chlorpyrifos, endosulfan, and imazalil;
   (b) 150 g/l to 400 g/l of the methyl ester of rosin;
   (c) 30 g/l to 200 g/l of at least one surfactant;
   (d) water to make up to one liter, but not less than 200 g/l; and
   (e) optionally up to 200 g/l of at least one polar solvent which is at least partially soluble in water.

2. A formulation in accordance with claim 1 wherein the pesticide is endosulfan.

3. A formulation in accordance with claim 1 wherein the pesticide is imazalil.

4. A formulation in accordance with claim 1 wherein the pesticide is chloropyrifos.

5. A formulation in accordance with claim 1, wherein the surfactant is chosen from the group consisting of ethoxylated castor oil and alkoxylated butyl alcohol.

6. A formulation in accordance with claim 1, wherein the surfactant is ethoxylated castor oil or ethoxylated propoxylated castor oil.

7. A formulation in accordance with claim 1 wherein the polar solvent is selected from the group consisting of propylene glycol, dipropylene glycol and polyglycol.

8. A formulation in accordance with claim 2, wherein the surfactant is chosen from the group consisting of ethoxylated castor oil and alkoxylated butyl alcohol.

9. A formulation in accordance with claim 3, wherein the surfactant is chosen from the group consisting of ethoxylated castor oil and alkoxylated butyl alcohol.

10. A formulation in accordance with claim 4, wherein the surfactant is chosen from the group consisting of ethoxylated castor oil and alkoxylated butyl alcohol.

11. A formulation in accordance with claim 2, wherein the surfactant is ethoxylated castor oil or ethoxylated propoxylated castor oil.

12. A formulation in accordance with claim 3, wherein the surfactant is ethoxylated castor oil or ethoxylated propoxylated castor oil.

13. A formulation in accordance with claim 4, wherein the surfactant is ethoxylated castor oil or ethoxylated propoxylated castor oil.

14. A formulation in accordance with claim 5, wherein the surfactant is ethoxylated castor oil or ethoxylated propoxylated castor oil.

15. A formulation in accordance with claim 8, wherein the surfactant is ethoxylated castor oil or ethoxylated propoxylated castor oil.

16. A formulation in accordance with claim 2 wherein the polar solvent is selected from the group consisting of propylene glycol, dipropylene glycol and polyglycol.

17. A formulation in accordance with claim 3 wherein the polar solvent is selected from the group consisting of propylene glycol, dipropylene glycol and polyglycol.

18. A formulation in accordance with claim 4 wherein the polar solvent is selected from the group consisting of propylene glycol, dipropylene glycol and polyglycol.

19. A formulation in accordance with claim 5 wherein the polar solvent is selected from the group consisting of propylene glycol, dipropylene glycol and polyglycol.

20. A formulation in accordance with claim 6 wherein the polar solvent is selected from the group consisting of propylene glycol, dipropylene glycol and polyglycol.

* * * * *